(12) United States Patent
Birmingham et al.

(10) Patent No.: US 8,518,029 B2
(45) Date of Patent: Aug. 27, 2013

(54) SCALP TREATMENT DEVICE

(75) Inventors: John Joseph Birmingham, Wirral (GB); Jason Shaun Burry, Wirral (GB); Ian Hopkinson, Wirral (GB); Graham Andrew Turner, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 476 days.

(21) Appl. No.: 12/288,583

(22) Filed: Oct. 22, 2008

(65) Prior Publication Data
US 2009/0270845 A1    Oct. 29, 2009

Related U.S. Application Data

(63) Continuation-in-part of application No. 12/150,034, filed on Apr. 24, 2008, now abandoned.

(51) Int. Cl.
*A61B 18/20* (2006.01)

(52) U.S. Cl.
USPC .............................................. 606/9; 607/88

(58) Field of Classification Search
USPC .............................. 607/88–94; 601/15; 606/9
See application file for complete search history.

(56) References Cited

U.S. PATENT DOCUMENTS

| | | | |
|---|---|---|---|
| 2,397,757 A | 4/1946 | Schwedersky | 128/395 |
| 5,030,090 A | 7/1991 | Maeda | |
| 5,300,097 A * | 4/1994 | Lerner et al. | 607/93 |
| 6,618,614 B1 * | 9/2003 | Chance | 600/473 |
| 2004/0097890 A1 * | 5/2004 | Wilkinson | 604/289 |
| 2005/0251242 A1 | 11/2005 | Bousfield | |
| 2006/0161226 A1 | 7/2006 | McMickle | |
| 2006/0247609 A1 * | 11/2006 | Mirkov et al. | 606/9 |
| 2006/0265028 A1 * | 11/2006 | Houle et al. | 607/88 |
| 2007/0149900 A1 * | 6/2007 | Lin | 601/15 |
| 2008/0072389 A1 * | 3/2008 | Ghosh et al. | 15/105 |
| 2008/0172112 A1 | 7/2008 | Gourgouliatos et al. | 607/89 |
| 2008/0172113 A1 | 7/2008 | Gourgouliatos et al. | 607/90 |

(Continued)

FOREIGN PATENT DOCUMENTS

| DE | 19513875 A1 | 10/1996 |
|---|---|---|
| DE | 102004017547 | 10/2005 |

(Continued)

OTHER PUBLICATIONS

PCT International Search Report in PCT application PCT/EP2008/0643305, Oct. 2008.
EP Search Report in EP application EP 07 10 6867, Apr. 2008.

*Primary Examiner* — Bill Thomson
*Assistant Examiner* — Jeffrey Lipitz
(74) *Attorney, Agent, or Firm* — Karen E. Klumas

(57) ABSTRACT

The invention provides a hand held hair treatment device for the stimulation of hair growth on the scalp, which device comprises:
a housing which includes a handle portion and a head portion;
a plurality of hollow tines, each tine having a proximal end affixed to the head portion, a longitudinal length extending from the head portion and a distal end terminating in a tip section;
a light source disposed within the housing and configured to output light;
light guide means for channelling the light from the light source through the tines and along a light guide means axis; and
optical devices which are located at the distal ends of the tines;
characterised in that the optical devices are configured to vector light which is incident upon them transversely to the general light guide means axis.

5 Claims, 2 Drawing Sheets

(56) References Cited

U.S. PATENT DOCUMENTS

| | | |
|---|---|---|
| 2008/0172115 A1 | 7/2008 | Gourgouliatos et al. ....... 607/94 |
| 2008/0177255 A1 | 7/2008 | Bernardini ........................ 606/3 |
| 2008/0215123 A1 | 9/2008 | Maricle et al. .................. 607/89 |

FOREIGN PATENT DOCUMENTS

| | | |
|---|---|---|
| WO | WO0160457 A1 | 8/2001 |
| WO | WO02102228 A2 | 12/2002 |
| WO | WO2005046793 A2 | 5/2005 |

* cited by examiner

SCALP TREATMENT DEVICE

This application is a continuation-in-part of U.S. patent application Ser. No. 12/150,034 filed on Apr. 24, 2008.

The present invention relates to a scalp treatment device, and more particularly to a hand held scalp treatment device using light for the stimulation of hair growth.

BACKGROUND AND PRIOR ART

Light biostimulation has been recognized as a method for providing stimulation to the scalp which has beneficial and therapeutic effects in terms of stimulating the natural growth of hair. For example, low level laser light is believed to enhance the physiological state of the scalp and encourage hair growth when radiated onto the hair follicles on the scalp. Non-coherent light sources such as light emitting diodes (LED) have also been described in this context.

A number of hand held devices have been designed to exploit the biostimulation effects of light sources such as low level laser and LED in a convenient and portable format.

WO01/60457 describes a hand-held, comb-like device emitting laser beams from laser diodes set in a row centred between two parallel rows of teeth for parting hair. The parting of the hair by the comb teeth is said to improve contact between the laser beam or beams and the scalp to be treated.

WO02/102228 describes a similar device, further including a stepped beam splitting reflector which splits one or more laser beams to allow a laser to simultaneously provide multiple laser beams which are distributed across a segment of an individual's scalp. The beam splitting reflector is mechanically aligned with the laser source and has a zigzag structure that mechanically deflects portions of the laser beam as it passes over the peaks of the beam splitting reflector. The portions of the laser beam form a line of reflected laser beams that project towards the users scalp.

In use, the devices described in WO01/60457 and WO02/102228 emit a narrow strip of parallel light beams from the comb housing onto the scalp. This produces a narrow strip of small, discrete beam spots on the surface under treatment. A problem associated with this pattern of scalp irradiation is that a proportion of the hair follicles present in the surface under treatment may be inadequately irradiated, or not irradiated at all, due to the size and spacing of the beam spots when applied to the scalp. This proportion may be especially significant in areas where the density of hair follicles is high. Repeated passage of the device over the area in question is not a satisfactory solution since there is an overall limit to the amount of laser power that can be applied to a person's scalp before the benefits of laser treatment are outweighed by more harmful conditions such as scalp redness, dryness and peeling.

The object of the present invention is to improve the pattern of scalp irradiation delivered from a hand held scalp treatment device using light for the stimulation of hair growth.

The invention solves the problem of uneven or inadequate scalp irradiation by means of a configuration which channels light through a plurality of hollow tines and spreads the light outwardly from the ends of the tines onto the surface of the scalp to be treated.

U.S. Pat. No. 5,303,722 describes a light comb including a plurality of comb teeth, a device for guiding light from a light source through the comb back into the comb teeth, and a device for radiating the light from the comb teeth. However, the purpose of the device of U.S. Pat. No. 5,303,722 is to selectively irradiate hair to be bleached which is located between the teeth of the comb, and not the scalp. Concave mirrors are used in the tips of the comb teeth to guide light away from the scalp and into the intermediate spaces between the comb teeth.

SUMMARY OF THE INVENTION

The present invention provides a hand held hair treatment device for the stimulation of hair growth on the scalp, which device comprises:

a housing which includes a handle portion and a head portion;

a plurality of hollow tines, each tine having a proximal end affixed to the head portion, a longitudinal length extending from the head portion and a distal end terminating in a tip section;

a light source disposed within the housing and configured to output light;

light guide means for channelling the light from the light source through the tines and preferably along a light guide means axis, and optical devices which are located at the distal ends of the tines;

characterised in that the optical devices are configured to spread light which is incident upon them in an outward direction from the distal ends of the tines to the surface of the scalp to be treated, or in a separate embodiment where the light is channelled from the light source through the tines and along a light guide means axis, to vector light which is incident upon them transversely to the general light guide means axis.

The handle portion may be any structure which facilitates gripping of the device by the user. For example, the handle portion may be formed by an elongated section of the housing, or alternatively may be a strap provided on the housing so that the device may be retained by the hand of the user.

The hollow tines serve to part the hair, enabling light to reach the surface of the scalp. The tines also provide the structures through which light is channelled by the light guide means. The longitudinal lengths of the tines may be formed from any material which enables the tines to perform these functions. Preferably the longitudinal lengths of the tines are formed from a substantially rigid material such as polypropylene, polyethylene, polyester, polycarbonate, polyvinylchloride or other material having similar characteristics.

The individual tines may have a longitudinal length ranging from 0.5 to 5 cm, preferably about 1 to 2 cm.

The individual tines may have a diameter ranging from 0.5 to 5 mm, preferably about 1 to 2 mm.

In an especially preferred embodiment, the tip sections of the tines are formed from a soft and flexible material (such as thermoplastic elastomer, rubber or other material having similar characteristics). This provides a pleasant feel when combing the user's hair or massaging the user's scalp. To this end, it is preferable to round the ends of the tip sections of the tines.

The tines are preferably arranged in a rectangular array of 1 to 3, preferably 2 to 3 rows.

The device may also include further tines in addition to those described above, which do not contain light. Such non-light containing tines may serve to assist in hair parting, scalp exposure, scalp massage or the like.

The device comprises a light source disposed within the housing and configured to output light. Suitable light sources include low power lasers, light emitting diodes or low power semiconductor lasers, capable of delivering light from the visible or infrared spectrum. Examples of preferred light sources are low power lasers having a wavelength ranging from about 600 nm to about 1000 nm, and an intensity ranging from about 1 mW/cm² to about 15 mW/cm². Such lasers are available commercially as complete modules which are small cylindrical units in which is encased the lasing medium which creates the laser beam and the electronics that control and process the electric current that passes through the lasing medium. Other preferred light sources are light emitting diodes having a wavelength ranging from about 620 to 690 nm, and an intensity ranging from about 1 mW/cm² to about 150 mW/cm².

The light source may deliver continuous or pulsed light, and may be powered by mains, battery or both. Battery power is advantageous for portability of the device. The battery can be rechargeable or disposable, preferably rechargeable.

Combinations, pluralities or assemblies of any of the above described light sources may also be used. For example, a plurality of laser modules as described above may be disposed in the housing at the proximal ends of the tines.

The light guide means serve to channel light from the housing and through the tines. Preferably the light guide means is constituted by a system of optical fibres which extends from the light source or sources, into the tines and through the tines. Suitable materials used to form the optical fibres may include fused silica, glass or an optical polymer such as polymethylmethacrylate. The optical fibres may extend singly through individual tines or may be provided in bundles.

The optical devices are configured to spread light incident upon them outwardly from the distal ends of the tines onto the surface of the scalp to be treated. By 'outwardly' is meant that the light beam is projected onto the scalp such that it passes outside the footprint of the tine on the scalp. In a preferred embodiment, an optical modifier diffuses the light from the general axis of the tine. This improves the coverage of the light on the scalp's surface and reduces the chances of the user burning the scalp by repeatedly combing over the same area.

The optical devices will typically include one or more optical components which are capable of spreading light incident upon them in a controlled manner in the desired direction(s), so that a light beam footprint of a predetermined shape is produced on the target surface. By "light beam footprint" is meant the area of the target surface irradiated by the light beam at any moment, or in other words, the intersection of the light beam with the target surface.

Examples of preferred optical components include lenses, optical fibres, mirrors, transparent materials, semi-transparent materials, prisms, reflective coatings, reflecting grooves, beam splitters, light channels or gratings.

Most preferably, the optical modifier is a lens.

Combinations, pluralities or assemblies of any of the above described optical components may also be used.

The optical devices are located at the distal ends of the tines. In order to optimize the pattern of scalp irradiation delivered from the device, it is preferred that the optical devices are located slightly upstream from the actual end points of the tines. This slight spacing ensures that the light which is spread from the distal ends of the tines by the optical devices is not "buried" in the soft scalp surface when the tines are applied to the scalp.

Accordingly, in a preferred tine construction, the optical devices are disposed in a region adjacent to the tip sections of the tines, in the direction of the head portion of the device.

Preferably, the optical modifier is disposed from 2 to 10 mm from the distal end of the tine, more preferably from 4 to 6 mm.

An especially preferred tine construction has a substantially rigid longitudinal length and a soft flexible tip section, with the optical device located at the interface between these two component parts.

The optical devices are configured to spread light outwardly from the distal ends of the tines onto the surface of the scalp to be treated. The optical devices serve to deliver an optimal pattern of irradiation to the target scalp surface. By "optimal pattern of irradiation" is generally meant a pattern in which the irradiation is spread over the target surface so that it covers at least 60%, preferably at least 80% of the total area of that target surface. Preferred patterns of irradiation have a regular or substantially regular spatial distribution.

In a preferred construction, the optical devices of the tines are configured so that they produce an array of circular light beam footprints on the target scalp surface. It is preferable to avoid a significant degree of overlap between individual footprints in the array. Accordingly, it is preferred that each individual footprint borders on those footprints which are adjacent to it in the array. The individual beam footprints could alternatively be square, polygonal, or any other shape suitable to deliver an optimal pattern of irradiation.

BRIEF DESCRIPTION OF THE DRAWINGS

Embodiments of the present invention will now be described with reference to the following non-limiting drawings in which.

DETAILED DESCRIPTION OF THE INVENTION

Figure 1:
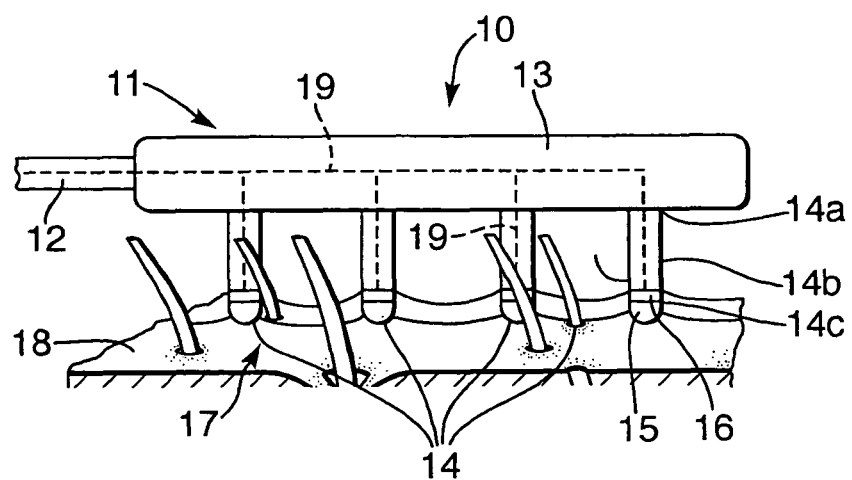
FIG. 1 depicts a partial schematic sectional view of a hair treatment device of the invention applied to the surface of the scalp.
Figure 2:
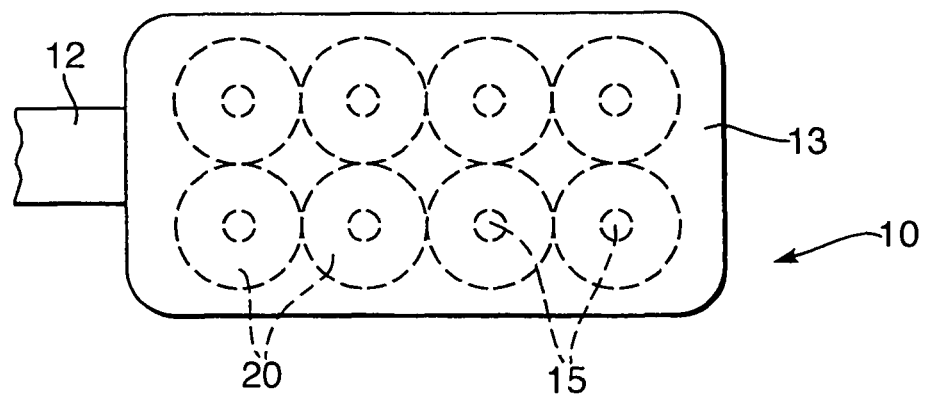
FIG. 2 depicts a partial schematic top planar view of the device of FIG. 1 in use, illustrating the pattern of light beam footprints produced by the device.
Figure 3:
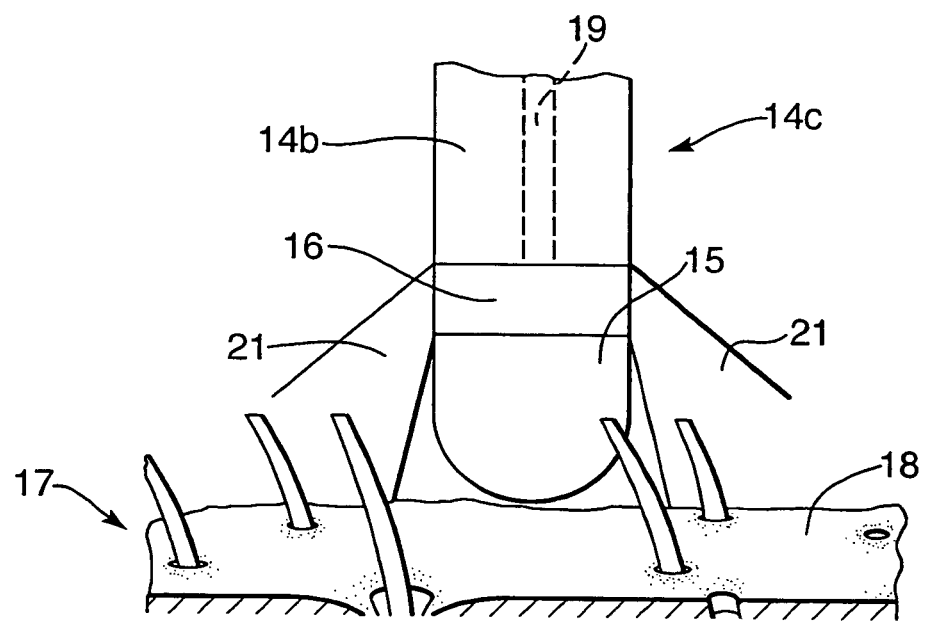
FIG. 3 depicts an enlarged schematic sectional view of the distal end of a tine of the device of FIG. 1 in use on the surface of the scalp.

As shown in FIGS. 1 to 3, a hair treatment device 10 has a housing 11 formed from a handle portion 12 (shown in part) which is connected to a head portion 13. Two parallel rows of four hollow tines 14 are connected to head portion 13 and project downward from head portion 13. Each individual tine 14 has a proximal end 14a affixed to head portion 13, a rigid longitudinal length 14b extending from head portion 13, and a distal end 14c. The distal ends 14c of the tines terminate in rounded soft flexible tip sections 15. Lens assemblies 16 are interposed between longitudinal lengths 14b and flexible tip sections 15.

In use, the device 10 is applied to an area of scalp 17, with the flexible tip sections 15 applied to the surface of the scalp 18. A system of fibre optics 19 channels light from a light source (not shown) through the handle portion 12, into the head portion 13, and down through each of the tines 14 towards lens assemblies 16. Light incident upon lens assemblies 16 is spread by lens assemblies 16 in an outward direction from the distal ends 14c of tines 14 onto the surface of the scalp 18. The light emerging from lens assemblies 16 (shown as 21 on FIG. 3) produces an array of circular light beam footprints (shown as 20 on FIG. 2) on the surface 18.

The invention claimed is:

1. A hand held hair treatment device for the stimulation of hair growth on the scalp, which device comprises:

a housing which includes a handle portion and a head portion;

a plurality of hollow tines, each tine having a proximal end affixed to the head portion, a longitudinal length extending from the head portion and a distal end terminating in a tip section formed from a soft and flexible material;

a light source disposed within the housing and configured to output light, wherein the light source is a low power laser having a wavelength ranging from about 600 nm to about 1000 nm, and an intensity ranging from about 1 mW/cm$^2$ to about 150 mW/cm$^2$, a light emitting diode having a wavelength ranging from about 620 to 690 nm, and an intensity ranging from about 1 mW/cm$^2$ to about 150 mW/cm$^2$, or a combination thereof;

light guide means for channelling the light from the light source through the tines and along a light guide means axis; and lenses which are located 2 to 10 mm from the distal ends of the tines;

characterised in that the lenses are configured to vector light which is incident upon them transversely to the general light guide means axis, spreading the light in an outward direction from the distal ends of the lines and upstream of the tip section.

2. A device according to claim I, in which the longitudinal lengths of the tines are formed from a substantially rigid material.

3. A device according to claim 1, in which the light guide means is constituted by a system of optical fibres which extends from the light source or sources, into the tines and through the tines.

4. A device according to claim 1, in which the lenses are configured so that they produce an array of circular light beam footprints on the target scalp surface.

5. A hand had hair treatment device for the stimulation of hair growth on the scalp, which device comprises:

a housing which includes a handle portion and a head portion;

a plurality of hollow tines, each tine having a proximal end affixed to the head portion, a longitudinal length extending from the head portion and a distal end terminating in a tip section formed from a soft and flexible material, wherein the longitudinal lengths of the tines are formed from a substantially rigid material;

a light source disposed within the housing and configured to output light, wherein the light source is a low power laser having a wavelength ranging from about 600 nm to about 1000 nm, and an intensity ranging from about 1 mW/cm$^2$ to about 150 mW/cm$^2$, a light emitting diode having a wavelength ranging from about 620 to 690 nm, and an intensity ranging from about 1 mW/cm$^2$ to about 150 mW/cm$^2$, or a combination thereof;

light guide means for channelling the light from the light source through the tines, and lenses which are located 2 to 10 mm from the distal ends of the tines;

characterized in that the lenses are configured to spread light which is incident upon them in an outward direction from the distal ends of the tines and upstream of the tip section, and onto the surface of the scalp to be treated.

* * * * *